United States Patent [19]

Shore

[11] Patent Number: 4,788,061
[45] Date of Patent: Nov. 29, 1988

[54] EXTENDED OCCLUSIVE TREATMENT OF SKIN DISORDERS

[76] Inventor: Ronald N. Shore, 9900 Georgia Ave., Silver Spring, Md. 20902

[21] Appl. No.: 752,406

[22] Filed: Jul. 5, 1985

[51] Int. Cl.$^4$ .............................................. A61L 15/06
[52] U.S. Cl. ..................................... 424/448; 424/78; 424/162; 514/43; 514/169; 514/249; 514/311; 514/550; 514/732; 514/762; 514/863; 514/953
[58] Field of Search .................. 424/448, 78; 514/953, 514/863

[56] References Cited

U.S. PATENT DOCUMENTS

| | | | |
|---|---|---|---|
| 3,043,745 | 7/1962 | Singer | 514/863 |
| 3,632,740 | 1/1972 | Robinson et al. | 424/28 |
| 3,749,784 | 7/1973 | Johnson | 514/863 |
| 3,896,789 | 7/1975 | Trancik | 424/448 X |
| 3,949,742 | 4/1976 | Nowakowski | 128/155 |
| 3,987,202 | 10/1976 | Okun | 424/331 |
| 4,073,291 | 2/1978 | Marvel et al. | 424/448 X |
| 4,181,725 | 1/1980 | Voorhees et al. | 514/863 |
| 4,210,633 | 7/1980 | Takruri | 424/80 |
| 4,325,965 | 4/1982 | Chiba | 514/863 |
| 4,341,783 | 7/1982 | Scheindlin | 514/863 |
| 4,486,450 | 12/1984 | Bernstein | 514/863 |
| 4,495,203 | 1/1985 | Grollier | 514/863 |
| 4,512,978 | 4/1985 | Inwood | 514/863 |
| 4,551,480 | 5/1985 | Stiefel | 514/863 |
| 4,569,935 | 2/1986 | Rosenberg et al. | 514/863 |

FOREIGN PATENT DOCUMENTS 272349 12/1963 Australia .
704754 3/1965 Canada .

OTHER PUBLICATIONS

Current Therapy in Dermatology, 1985, Provost et al, pp. 21–23, 37–39, 249–251.
Friedman, Arch. Dermatol. vol. 123, Aug. 1987, pp. 1046–1052.
Skin and Allergy News, vol. 16, No. 2, Feb. 1985, p. 2.
New England Journal of Medicine, vol. 312, Jan. 24, 1985, p. 246.
New York Times, Science Watch, Feb. 5, 1985.
Washington Post, Health Section, vol. 1, No. 5, Feb. 6, 1985, p. 5.
British Journal of Dermatology, vol. 82, pp. 458–462 (1970).
Dermatology in General Medicine, Part III, Chapter 8, "Psoriasis", p. 226 (1971).
Archives of Dermatology, vol. 117, pp. 388–393, Jul. 1981.
Journal of The American Academy of Dermatology, vol. 11, No. 1, p. 37, Jul. 1984.
Archives of Dermatology, vol. 120, No. 5, pp. 625–630, May 1984.
Journal of The American Academy of Dermatology, vol. 12, No. 4, pp. 100A–102A, Apr. 1985.
Arndt, Kenneth A, Manual of Dermatologic Therapeutics, 3d Edn., pp. 141–150, 271–275 (Little, Brown & Co. 1983).
Physicians Desk Reference (PDR) 39th Edn., p. 897 (1985).
Cutis, vol. 29, No. 6, pp. 646–649, Jun. 1982.
Journal of The American Academy of Dermatology, vol. 4, No. 1, pp. 1–14, Jan. 1981.
Supplement to the Journal of The American Academy of Dermatology, vol. 11, No. 5, part 2, pp. 937–947, Nov. 1984.

*Primary Examiner*—Leonard Schenkman
*Attorney, Agent, or Firm*—Berman, Aisenberg & Platt

[57] ABSTRACT

The healing of a number of skin disorders is effectively enhanced by prolonged continuous occlusion and/or hydration. Treating these disorders, e.g. psoriasis, is significantly facilitated by occluding affected skin areas with a suitable barrier for a prolonged and continuous period of time. Such occlusion is effective by itself, but is materially improved by concurrent topical administration of medicament useful for treating the disorder. In such cases the prolonged, continuous occlusion markedly increases hydration which has the further therapeutic benefit of tremendously facilitating penetration of medicament. The provided barrier is advantageously one with low vapor transmission or one which is water impermeable.

25 Claims, No Drawings

EXTENDED OCCLUSIVE TREATMENT OF SKIN DISORDERS

FIELD OF THE INVENTION

Occluding psoriatic lesions for an extended period of time can abate or relieve the symptoms of, alleviate the stress and suffering caused by and even heal such lesions. The noted beneficial effects are enhanced by concurrent application of medicament useful for treating psoriasis. The same approach is also useful for treating other skin disorders.

BACKGROUND

Emil G. Klarman confirmed (Burger, A., "Medicinal Chemistry", second edition, page 1147, Interscience Publishers, Inc., New York, 1960) that there is no known cure for psoriasis, but "different therapeutic agents may produce involution of psoriatic lesions." Although occlusion of psoriatic lesions with an impermeable barrier is known to decrease the high mitotic rate of epidermal basal cells and to cause reformation of the granular cell layer (Fry, L., Almeyda, J., McMinn, R. M. H., "Effect of Plastic Occlusive Dressings on Psoriatic Epidermis", Br. J. Dermatol., 82, 458 to 462, 1970), patients with psoriasis, when applying adhesive tape, are warned "that its removal may traumatize the epidermis sufficiently to evoke an isomorphic lesion" (Van Scott, Eugene J. and Farber, Eugene M., "Dermatology in General Medicine," Chapter 8, page 226, McGraw-Hill Book Company, 1971).

Psoriasis affects about 2 percent of the American population. The great majority of these so affected have minimal skin involvement (less than 10 to 15 percent of the skin surface), which is still sufficient to produce severe physical discomfort and psychological effects in many patients (Weinstein, Gerald D., et al., "A Clinical Screening Program for Topical Chemotherapeutic Drugs in Psoriasis", Arch. Dermatol., Vol. 117, pp. 388,293, July, 1981). Their clinical testing involved application of test agents to psoriatic plaques under occlusion daily for up to nine days.

Williamson found that clearing of resistant plaques with anthralin was significantly enhanced by using an occlusive dressing (occluded for 12 hours daily with PVC film), but irritant side effects were increased (Coskey, Ralph J., "Dermatologic Therapy, December 1982, through November, 1982", Journal of the American Academy of Dermatology, Vol. 11, No. 1, pages 25 to 52, at 37, July, 1984). By instructing patients to cover nightly anthralin paste applications with semipermeable paper tape, a practical method for out-patient therapy was devised (Pearlman, Dale L., et al., "Paper-Tape Occlusion of Anthralin Paste", Arch. Dermatol, Vol. 120, No. 5, pp. 625-630, May, 1984).

An advertisement for Diprolene Ointment for treating psoriasis has a specific instruction not to use an occlusive dressing (Journal of the American Academy of Dermatology, Vol. 12, No. 4, 101A, April, 1985).

In a chaper on psoriasis, Arndt, Kenneth A. ("Manual of Dermatologic Therapeutics", third edition, pp. 143, Little, Brown and Company, 1983) states that overnight or 24-hour occlusive therapy with Cordran Tape will initiate involution in most lesions, and corticosteroids exert their beneficial effects in this setting as mitotic inhibitors. Although the same text points out undesirable effects from occlusive therapy (page 272), it asserts that occlusive (airtight) dressings increase the efficacy of cream preparations in treating psoriasis (page 274).

A medicated adhesive tape for treating psoriasis is being marketed. The "Physicians' Desk Reference" (PDR), 39th edition, page 897, 1985, provides the following information:

"Cordran Tape is a transparent, inconspicuous, plastic surgical tape, impervious to moisture. It contains . . . (flurandrenolide, Dista), a potent corticosteriod for topical use . . .

"Each square centimeter contains 4 mg of flurandrenolide uniformly distributed in the adhesive layer. The tape is made of a thin, matte-finish polyethylene film which is slightly elastic and highly flexible.

"The adhesive is a synthetic copolymer of acrylate ester and acrylic acid which is free from substances of plant origin. The pressure-sensitive adhesive surface is covered with a protective paper liner to permit handling and trimming before application . . .

"The tape serves as both a vehicle and an occlusive dressing. Retention of insensible perspiration by the tape results in hydration of the stratum corneum and improved diffusion of the medication. The skin is protected from scratching, rubbing, desiccation, and chemical irritation. The tape acts as a mechanical splint to fissured skin. Since it prevents removal fo the medication by washing or the rubbing action of clothing, the tape formulation provides a sustained action . . .

The directions for use state: "Replacement of the tape every twelve hours produces the lowest incidence of adverse reactions; but it may be left in place for twenty-four hours if it is well tolerated and adheres satisfactorily."

SUMMARY OF THE INVENTION

In direct conflict with standard accepted approach of daily (or more frequent) dressing changes in the topical treatment of dermatologic diseases, this invention requires occluding affected skin areas by continuously maintaining a tight barrier thereover for a period of at least three days. The tight barrier is, e.g., in the form of an adhesive tape which optionally has suitable topical medication on its adhesive surface. An object of this invention is to abate or relieve the symptoms of, alleviate distress and suffering caused by and to heal skin disorders, e.g. psoriatic lesions.

Prolonged (i.e. for at least 3 days) continuous occlusion (by itself or in conjunction with medication) has not been previously appreciated (by the medical community) as effective therapy for clearing psoriasis. Even though occlusion has been used on a daily or more frequent basis to enhance penetration of topical agents, the value of prolonged, continuous, tight occlusion was neither recognized nor employed therapeutically by physicians for healing and clearing psoriasis.

Although this invention is primarily concerned with treatment of psoriasis, it is not so limited. The prolonged occlusive therapy is also effective for other difficult-to-treat skin problems, such as keloids (i.e., thick raised scars), fissured hand dermatitis, granuloma annulare, lichen planus, calluses, parapsoriasis and other thickened-skin disorders (well known to practicing dermatologists) for which occlusion enhances medicament, e.g., steroid, penetration and/or hydration positively aids the healing process. When a corticosteroid is concurrently applied topically, prolonged occlusion enhances penetration of the drug in all such cases and provides significant hydration. This therapy is far more effective than, e.g., plastic gloves, which do not provide continuous tight occlusion on all injured parts of the hands.

DETAILS

The mere continuous maintenance of, e.g., adhesive tape in tight contact with and over a skin surface afflicted with psoriasis (or other skin disorder for which hydration positively aids the healing process) for a period of at least three days results in noticeable improvement, including clearing of the skin and alleviation of the stress and suffering caused by thus-occluded lesions. When an adhesive tape is employed, the tape is, optionally, of any suitable material, such as paper, fabric (cotton or synthetic), or plastic film. There is a significant advantage to having a water-proof tape of at least one with low vapor transmission which will result in substantial skin hydration, but this is not absolutely essential for at least one aspect of the present invention. The tape should be flexible so that it will conform to the surface to which it is applied and, preferably, accommodate movement of limbs to which it is secured; it should be able to stretch and is advantageously elastomeric.

The adhesive is necessarily one which is capable of maintaining the tape secured to human skin for a period of at least three days. It also must be one which does not irritate the surface to which it is applied. When employed tape contains medicament on its surface, the adhesive must also be one which is inert to or, at least, does not adversely react with such medicament. Whether or not any other medicament is used on or in conjunction with adhesive tape, the tape advantageously contains (on the skin-facing surface) a component, such as zinc oxide, which suppresses overgrowth of skin bacteria and associated odor due to marked hydrating effects of tape applied continually for several days or longer.

Throughout this disclosure reference is made specifically to psoriasis and to psoriatic lesions. All such reference are equally applicable to other skin disorders for which occlusion enhances medicament penetration and/or hydration positively aids the healing process. When occlusive therapy is combined with topical medicament administration, the hydration further enhances drug penetration and effectiveness.

The invention is not in the tape (generically), the adhesive and/or the specific medicament that is optionally applied under the tape and/or incorporated in the adhesive. The invention lies in tightly occluding psoriatic lesions (or skin affected by some other disorder for which hydration positively aids the healing process and/or for which occlusion enhances medicament penetration) for a continuous period of at least three days and extending to, e.g., from one to three weeks. (This procedure, by itself, occasionally results in total clearing of covered lesions. The same procedure, however, is relatively ineffective when the tape is changed daily or more frequently.) This is effected by covering, e.g., psoriatic lesions on a skin surface with an adhesive tape and maintaining the adhesive tape in place for the noted period of time. As indicated, the adhesive must be one which is capable of maintaining the tape in place and in tight occlusion for the desired duration. The process is enhanced by providing the adhesive side of the tape with medicament useful for treating psoriasis. The medicament is optionally coated on or incorporated in the adhesive, but in an amount which does not prevent the adhesive from maintaining the tape secured to the skin for the desired period. Alternatively, such medicament is applied, e.g., directly to the psoriatic lesions prior to applying adhesive tape thereover.

Although tape (generally) is not a critical part of this invention, tape having a combination of the following properties: (a) water proof or permitting only low water vapor transmission, (b) sufficiently strong adhesion to maintain it in place on skin for at least one week, (c) flexibility, (d) elasticity and (e) an agent on the adhesive surface to suppress bacterial overgrowth, is novel and comprises one aspect of the invention. How to achieve each of these properties is well known; prior to this invention there was no reason to incorporate all such properties in a single tape.

The medicament is optionally virtually any medicament suitable for treating psoriasis. It is, e.g., an adrenocorticosteroid, such as amcinonide or fluocinonide. Alternatively, it is, e.g., anthralin, azauridine, chrysarobin, ichthammol, indochlorhydroxyquin, a mercury compound, methotrexate, resorcinol, selenium sulfide, or undecylenic acid. The only limitation of the amount of any selected medicament is that the concentration applied to any portion of the skin be less than that which will cause any adverse affect during the period to which the occlusion is continuously maintained. The bulk of applied medicament should also be less than that which would interfere with tight occlusion of tape or other barrier thereover.

The occlusion is preferably with an impermeable (primarily water-impermeable) barrier or one with low vapor transmission which will result in substantial hydration of occluded skin. The use of an adhesive tape is not absolutely essential. A sprayable liquid (water-proof glue) which solidifies on skin to form a barrier is useful by itself or directly over suitable medicament applied to psoriatic lesions. Tightly wrapping affected surface areas with a water-impermeable plastic film and sealing the edges with tape also provides beneficial results in the treatment of psoriasis when the film is similarly maintained in such position for at least three days. Sealing of the edges of such film is preferred, but not completely necessary. It is important to prevent moisture from leaving the skin surface. The tight wrapping of a plastic film over any particular area of affected skin is accomplished in any suitable manner, depending upon the particular area of skin involved.

When medicament is applied to a skin disorder prior to occlusion, it is advantageously applied in a very thin layer so as to avoid interference with tight occlusion of any dressing applied thereover.

Observation of total clearing at sites of adherent portions of a Band-Aid maintained on a psoriatic plaque (well-defined erythematous, scaly plaque on an elbow) for three weeks and no clearing of plaque covered by the Band-Aid pad led to experiments which confirm the effectiveness of tight occlusion for a continuous and extended period of time in treating psoriasis. Maintaining adhesive tape continuously for three weeks on remaining plaques on both elbows resulted in clearing those lesions as well. Shore, R.N., "Clearing of Psoriatic Lesions after the Application of Tape", *New England Journal of Medicine,* 312:246, 1985.

Prolonged application of water-proof adhesive tape over a potent topical corticosteroid, e.g. amcinonide ointment, yields particularly good results—forty-two of seventy-five treated lesions (56%) cleared entirely, and an additional fifteen lesions (20%) cleared except for erythema; sixty-two percent of the lesions (which cleared) stayed clear for one month or longer. This effective topical treatment is not messy, time-consuming or expensive. The amcinonide is optionally replaced with virtually any other topical medicament for treating psoriasis. The medicament is optionally incorporated in or on the adhesive of the adhesive tape or applied directly to the psoriatic lesions subsequently occluded by adhesive tape. When medicament is employed, care should be taken not to apply it in a mass sufficient to interfere with the tight occlusion of the barrier provided thereover.

Adhesive tapes continuously maintained in direct contact with psoriatic lesions or separated therefrom only by medicament for a period of one week or longer produced substantially better results than similar adhesive tape left on for only one or two days. Furthermore, a single prolonged application, such as for ten days, is far superior to multiple applications, such as ten applications of one day each. Such single prolonged application was first presented by Ronald N. Shore, M.D., at the annual meeting of the American Academy of Dermatology, Washington, D.C., Dec. 5, 1984.

Adhesive tapes with low water-vapor transmission and sufficient adhesive properties to maintain them firmly attached to skin for adequate lengths of time (e.g., from 1 to 3 weeks) are readily formed. Several are marketed, e.g., by Johnson & Johnson, but these do not possess all of the previously-noted properties.

Water-proof tape of Johnson & Johnson applied directly to psoriatic lesions continuously for one week resulted in total clearing of six of fifteen treated lesions (40 percent). Most of these cleared lesions remained cleared during several months of follow-up without additional treatment.

As complete resolution of psoriatic lesions was achieved for only 40% of lesions treated with waterproof tape alone, an attempt was made to achieve total clearing more frequently by combining such therapy with other topical therapy in order to develop a treatment that would be more effective for out-patient use. Separate tests with three topical agents: (1) amcinonide (Cyclocort) ointment, a Class 1 corticosteroid, (2) 0.1% anthralin (Drithocreme), and (3) 1.6% coal tar (Fototar) cream, with continuous occlusion for three-week test periods demonstrated that the tape-corticosteroid combination was clearly superior to the other two. Relatively low concentrations of anthralin and coal tar were tested because of concern that irritation might occur if higher concentrations were to be used with prolonged occlusion. The tape-amcinonide combination was the only one that produced total clearing within the study period. Accordingly, the water-proof tape/amcinonideointment combination was selected for further evaluation. Johnson & Johnson's Water-proof Tape was applied over amcinonide ointment in 75 lesions of 17 patients with chronic plaque psoriasis to assess the efficacy of this therapy. Most lesions were located on elbows and knees, but lesions elsewhere on the extremities and trunk were also treated. The tape was left on continuously for from one to three weeks, except for a few instances in which it came off prematurely. The corticosteroid and tape were reapplied one or two additional times if needed.

Forty-two lesions (56%) were thus totally cleared (total resolution of lesion with absence of erythema); fifteen lesions (20%) were almost cleared (lesion macular—flat—with residual erythema); fifteen lesions (20%) were improved; three lesions (4%) did not change. These results indicate that this is an extremely effective out-patient topical therapy. Lesions which cleared completely generally took two to three weeks to do so, but some cleared in as quickly as ten days. Five of the seventeen patients (29%) experienced clearing of every lesion treated. This degree of clearing is many times greater than that which has been reported for amcinonide ointment alone. Engel (Treatment of Psoriasis with Amcinonide 0.1% and Fluocinonide 0.05% Ointments. A Comparative Double-blind Study, Cutis 29:646–649 1982) reported total clearing in only one of twenty-six patients (4%) using amcinonide ointment twice a day for a three-week period.

Even when relatively good results are achieved with potent topical corticosteroids, there is almost always a prompt recurrence when the medication is stopped (Cram, D. L., Psoriasis: Current Advances In Etiology and Treatment. *J. Am. Acad. Dermatol.*, 4:1–14, 1981; Krueger, G. G., Bergstresser, P. R., Lowe, M. J., et al., Psoriasis, *J. Am. Acad. Dermatol.*, 11:937–47 1984). In complete contrast, sixty-two percent of the lesions (which cleared) stayed clear for one month or more, and in several cases there has been no evidence of recurrence after a period of from seven to nine months of follow-up. Regarding the duration of remission as that period of time before first signs of recurrence appears, sixteen of the lesions (38%) had a duration of remission of from one to four weeks; ten lesions (24%) had a duration of remission of from five to eight weeks, and sixteen lesions (38%) had a duration of remission of nine weeks or more.

In the same seventeen patients treated with waterproof tape and amcinonide ointment, more than seventy-five lesions were left untreated during the study period. None of these lesions showed spontaneous resolution.

With regard to the seventy-five lesions thus treated, some patients experienced side effects. With regard to four patients (24%) there was irritation from tape; with regard to two patients (12%) there was mild reversible atrophy of treated lesions; and with regard to one patient (6%) there was a skin infection. Irritation reactions were mild and tended to occur at the edge of the tape. These cleared in a few days with additional application of amcinonide ointment. Barely discernable atrophy was observed in lesions of two patients. In these cases, the corticosteroid component of the combination was temporarily discontinued and the signs of atrophy resolved. One patient developed a bacterial infection under the tape; this cleared without complication. No cases of miliaria or folliculitis were encountered in any of the seventeen patients.

When medicament is employed in combination with occlusion, such medicament is preferably in ointment, rather than in cream, form. Before adhesive tape and medicament are reapplied, involved areas should be washed well. Soaking for thirty minutes or more, immediately before retreatment, is particularly helpful on more resistant sites. Fissures and pustular psoriasis lesions tend to respond particularly well to this therapy. Even when such lesions are not totally eradicated, there is usually such improvement and relief of discomfort that patients are enormously grateful.

Prolonged occlusion therapy has advantages over other topical psoriasis treatments. Total clearing and remission is possible and frequent, which is certainly not true with topical corticosteroids alone, currently the most popular out-patient treatment for psoriasis. There is no staining, no mess and no odor from medications. Because medication is applied infrequently, it is very economical.

Those patients with minimal (less than 10 to 15% of the surface) skin involvement, i.e., the great majority of patients with psoriasis, would benefit most from this therapy. Patients with relatively small numbers of plaques (mainly on the trunk and extremities) are particularly good candidates.

The invention and its advantages are readily understood from the preceding description. Various changes may be made in the process, in the tape, in the adhesive, and/or medicament employed without departing from the spirit and scope of the invention or sacrificing its material advantages. The process and materials hereinbefore described are merely illustrative of preferred embodiments of the invention.

What is claimed is:

1. A process for treating a skin disorder for which healing or improvement is significantly aided by occlusion and/or hydration which comprises tightly occluding affected skin continuously for a period of at least three days.

2. A process according to claim 1 wherein the period is at least one week.

3. A process according to claim 1 wherein occlusion is with a water-impermeable barrier or a barrier with low vapor transmission which results in substantial skin hydration.

4. A process according to claim 3 wherein the barrier is adhesive tape.

5. A process according to claim 1 wherein occlusion is effected with closely adhering adhesive tape applied directly on skin affected with psoriasis.

6. A process according to claim 1 which comprises applying to the affected skin a topical medicament useful for treating the disorder and tightly occluding the medicated skin for a continuous period of at least three days.

7. A process according to claim 6 wherein tight occlusion is effected with adhesive tape applied directly on affected skin and wherein the adhesive tape has an adhesive side which comprises the topical medicament.

8. A process according to claim 6 or claim 7 wherein the medicament comprises a corticosteroid.

9. A process according to claim 6 or claim 7 wherein the medicament comprises anthralin.

10. A process according to claim 6 or claim 7 wherein the medicament comprises azauridine.

11. A process according to claim 6 or claim 7 wherein the medicament comprises chrysarobin.

12. A process according to claim 6 or claim 7 wherein the medicament comprises ichthammol.

13. A process according to claim 6 or claim 7 wherein the medicament comprises iodochlorhydroxyquin.

14. A process according to claim 6 or claim 7 wherein the medicament comprises a mercury compound.

15. A process according to claim 6 or claim 7 wherein the medicament comprises methotrexate.

16. A process according to claim 6 or claim 7 wherein the medicament comprises resorcinol.

17. A process according to claim 6 or claim 7 wherein the medicament comprises selenium sulfide.

18. A process according to claim 6 or claim 7 wherein the medicament comprises undecylenic acid.

19. A process according to claim 6 or claim 7 wherein the medicament comprises wood or coal tar.

20. A process according to claim 7 wherein the adhesive tape has an adhesive side which comprises amcinonide substantially uniformly spread thereover in a concentration which is effective to enhance and/or accelerate remission of the psoriasis or other skin disorder to which the tape is adhered.

21. A process according to claim 6 wherein the disorder is psoriasis, tightly occluding is effected with adhesive tape applied directly on skin affected with psoriasis and wherein the adhesive tape has an adhesive side which comprises the topical medicament.

22. A process for treating a skin disorder for which healing or improvement is significantly aided by occlusion and/or hydration which comprises tightly occluding affected skin continuously for a period of at least three days and wherein occlusion is effected with closely adhering adhesive tape which has low water-vapor transmission, which is flexible and elastic, which has adhesive with sufficient holding strength to maintain the tape in place on skin for a period of at least one week and wherein the tape has an adhesive surface comprising an agent which suppresses bacterial overgrowth.

23. A process according to claim 22 wherein the adhesive tape is waterproof.

24. A process according to claim 23 wherein the adhesive surface comprises medicament for treating psoriasis.

25. A process for treating a skin disorder for which healing or improvement is significantly aided by occlusion and/or hydration which comprises tightly occluding affected skin continuously for a period of at least three days and wherein occlusion is effected with closely adhering adhesive tape which has low water-vapor transmission, which is flexible and elastic, which has adhesive with sufficient holding strength to maintain the tape in place on skin for a period of at least one week and wherein the tape has an adhesive surface comprising topical medicament for treating psoriasis.

* * * * *

UNITED STATES PATENT AND TRADEMARK OFFICE
CERTIFICATE OF CORRECTION

PATENT NO. : 4,788,061
DATED : November 29, 1988
INVENTOR(S) : Ronald N. Shore

It is certified that error appears in the above-identified patent and that said Letters Patent are hereby corrected as shown below:

Column 2, line 26, "fo" should read --of--. Column 3, line 16, "of" should read --or--. Column 4, line 19, "indochlorhydroxyquin" should read --iodochlorhydroxyquin--. Column 7, line 20, "sided" should read --aided--.

Signed and Sealed this

Eleventh Day of April, 1989

Attest:

DONALD J. QUIGG

Attesting Officer

Commissioner of Patents and Trademarks